(12) United States Patent
Coelingh Bennink et al.

(10) Patent No.: US 9,034,854 B2
(45) Date of Patent: May 19, 2015

(54) PHARMACEUTICAL COMPOSITION COMPRISING ESTETROL DERIVATIVES FOR USE IN CANCER THERAPY

(75) Inventors: Herman Jan Tijmen Coelingh Bennink, Driebergen (NL); Evert Johannes Bunschoten, Heesch (NL)

(73) Assignee: PANTARHEI BIOSCIENCE B.V., Zeist (NL)

( * ) Notice: Subject to any disclaimer, the term of this patent is extended or adjusted under 35 U.S.C. 154(b) by 1466 days.

(21) Appl. No.: 10/521,040

(22) PCT Filed: Jul. 11, 2003

(86) PCT No.: PCT/NL03/00513
§ 371 (c)(1),
(2), (4) Date: Aug. 16, 2005

(87) PCT Pub. No.: WO2004/006936
PCT Pub. Date: Jan. 22, 2004

(65) Prior Publication Data
US 2006/0063723 A1 Mar. 23, 2006

(30) Foreign Application Priority Data

Jul. 12, 2002 (EP) .................................... 02077812
Feb. 14, 2003 (EP) .................................... 03075435

(51) Int. Cl.
*A01N 45/00* (2006.01)
*A61K 31/56* (2006.01)
*A61K 45/06* (2006.01)
*A61K 31/565* (2006.01)

(52) U.S. Cl.
CPC ............... *A61K 45/06* (2013.01); *A61K 31/565* (2013.01)

(58) Field of Classification Search
USPC .................................................. 514/169, 171
See application file for complete search history.

(56) References Cited

U.S. PATENT DOCUMENTS

| | | |
|---|---|---|
| 3,440,320 A | 4/1969 | Sackler et al. |
| 3,797,494 A | 3/1974 | Zaffaroni |
| 4,460,372 A | 7/1984 | Campbell et al. |
| 4,573,996 A | 3/1986 | Kwiatek et al. |
| 4,624,665 A | 11/1986 | Nuwayser |
| 4,722,941 A | 2/1988 | Eckert et al. |
| 4,762,717 A | 8/1988 | Crowley, Jr. |
| 4,937,238 A | 6/1990 | Lemon |
| 5,063,507 A | 11/1991 | Lindsey et al. |
| 5,130,137 A | 7/1992 | Crowley, Jr. |
| 5,211,952 A * | 5/1993 | Spicer et al. .................. 424/426 |
| 5,223,261 A | 6/1993 | Nelson et al. |
| 5,340,584 A * | 8/1994 | Spicer et al. .................. 424/426 |
| 5,340,585 A | 8/1994 | Pike et al. |
| 5,340,586 A | 8/1994 | Pike et al. |
| 5,468,736 A | 11/1995 | Hodgen |
| 5,633,242 A | 5/1997 | Oettel et al. |
| 5,662,927 A | 9/1997 | Ehrlich et al. |

(Continued)

FOREIGN PATENT DOCUMENTS

| | | |
|---|---|---|
| DE | 2336433 A1 | 4/1975 |
| DE | 2336434 A1 | 4/1975 |

(Continued)

OTHER PUBLICATIONS

National Cancer Institute: Breast cancer prevention retrieved online Aug. 7, 2007 from the internet http://www.cancer.gov/templates/doc.aspx?viewed=D972A74B-D25A-4F86-B8ED-33EB3C0450E4&version, p. 1.*

(Continued)

*Primary Examiner* — Mina Haghighatian
*Assistant Examiner* — Helen Chui
(74) *Attorney, Agent, or Firm* — Foley & Lardner LLP; Gilberto M. Villacorta; Sunit Talapatra

(57) ABSTRACT

The present invention relates to a method of treating or preventing estrogen-sensitive tumors in a mammal, said method comprising the administration of a therapeutically effective amount of an estrogenic component to said mammal, wherein the estrogenic component is selected from the group consisting of:

substances represented by the following formula

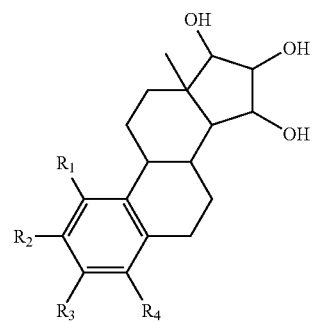

in which formula $R_1$, $R_2$, $R_3$, $R_4$ independently are a hydrogen atom, a hydroxyl group or an alkoxy group with 1-5 carbon atoms; precursors capable of liberating a substance according to the aforementioned formula when used in the present method; and mixtures of one or more of the aforementioned substances and/or precursors.

The estrogenic component according to the invention does not have undesirable proliferative effects on breast and/or endometrial tissue and displays sufficient estrogenicity to prevent that its administration will lead to hypoestrogenism and/or climacteric complaints.

27 Claims, 2 Drawing Sheets

(56) References Cited

U.S. PATENT DOCUMENTS

| | | | |
|---|---|---|---|
| 5,827,843 | A | 10/1998 | Koninckx |
| 6,214,815 | B1 | 4/2001 | Shangold et al. |
| 6,500,814 | B1 | 12/2002 | Hesch |
| 2002/0156059 | A1* | 10/2002 | Elliesen .................. 514/182 |
| 2002/0183299 | A1 | 12/2002 | Voskuhl |

FOREIGN PATENT DOCUMENTS

| | | |
|---|---|---|
| DE | 2426779 A1 | 12/1975 |
| DE | 19917930 A1 | 10/2000 |
| EP | 0402950 A | 12/1975 |
| EP | 468690 A1 | 7/1991 |
| EP | 1700602 A1 | 5/2001 |
| WO | 9603929 A1 | 2/1966 |
| WO | 9218107 A1 | 10/1992 |
| WO | WO 94/26207 | 11/1994 |
| WO | 9502408 A1 | 1/1995 |
| WO | 9517895 | 7/1995 |
| WO | 9603929 A1 | 2/1996 |
| WO | 9858657 A1 | 12/1998 |
| WO | 0062753 | 10/2000 |
| WO | 0073416 A1 | 12/2000 |
| WO | 0130357 A | 5/2001 |
| WO | 0185154 A2 | 11/2001 |
| WO | WO 02/30355 * | 4/2002 |
| WO | WO 02/094276 A1 | 11/2002 |
| WO | WO 02/100877 A1 | 12/2002 |

OTHER PUBLICATIONS

Medline Plusâ: Medical Encyclopedia: Ovarian cancer retrieved online on Aug. 9, 2007 from the internet https://www.nlm.nih.gov/medlineplus/ovariancancer.html, p. 1 dated on Jul. 31, 2007.*
National Cancer Institute: Breast Cancer Prevention retrieved online Aug. 7, 2007 from the internet http://www.cancer.gov/cancertopics/pdq/prevention/breast/Patient/page 3.*
Zips et al. in vivo, 2005, 19:1-8.*
Holinka et al. Biology of Reproduction, 1980, 22, 913-926.*
Holinka et al. (Biology of reproduction, 1980: 22, 913-926).*
U.S. Appl. No. 10/532,320, Jun. 2006, Bennink et al.*
National Cancer Institute: Breast cancer prevention retrieved online Aug. 7, 2007 from the internet http://www.cancergov/templates/doc.aspx?viewed=D972A74B-D25A-4F86-B8ED-33EB3C0450E4&version, p. 1.*
Medline Plus : Medical Encyclopedia: Ovarian cancer retrieved online on Aug. 9, 2007 from the internet https://www.nlm.nih.gov/medlineplus/ovariancancer.html, p. 1 dated on Jul. 31, 2007.*
National Institute of Child Health and Human development, NIH Publication No. 02-2413 retrieved online on Aug. 9, 2007.*
Breast Cancer Prevention retrieved online Aug. 7, 2007 from the internet http://www.cancer.gov/cancertopics/pdq/prevention/breast/Patient/page 3.*
Prophylactic definition—Medical Dictionary of Popular Medical Terms: retrieved on Mar. 14, 2008 via www.medterms.com/script/main/art.asp?articlekey=11902.*
U.S. Appl. No. 10/557,549, May 2006, Bennink et al.*
Mayo Clinic: Benign Prostatic Hyperplasia.*
Mayo Clinic: Melanoma Treatments 1-3.*
Martucci et al., "Impact of Continuously Administered Catechol Estrogens on Uterine Growth and Luteinizing Hormone Secretion", Endocrinology (Dec. 1979), vol. 105, No. 6, pp. 1288-1292.
Weigert et al., "Comparison of Stimulation with Clomiphenes Citrate in Combination with Recombinant Follicle Stimulating Hormone and Recombinant Luteinizing Hormone to Stimulation with a Gonadotropin-Releasing Hormone Agonist Protocol: A Prospective Randomized Study", Fertility and Sterility, (Jul. 2002), vol. 78, No. 1, pp. 34-39.
Trotter et al., "Effects of Postnatal Estradiol and Progesterone Replacement in Extremely Preterm Infants", J. Clin. Endocrinol Metab., (Dec. 1999), vol. 84, No. 12, pp. 4531-5.
Shanklin et al., "Aqueous Estrogens in the Management of Respiratory Distress SYndrome", J. Reprod. Med. (Aug. 1970), vol. 5, No. 2, pp. 53-71.
Chemical Abstracts Service, Columbus Ohio, US: Jakowicki, "Evaluation of Estriol Level in the Amniotic Fluid in Prolonged Pregnancy", XP002458625.
Gorwill et al., "Unconjugated Serum Oestriol Levels in Mother and Baby with Meconium Staining of the Amniotic Fluid", Br. J. Obstet. Gynaecol. (Aug. 1978), vol. 85, No. 8, pp. 602-4.
Fogary, Jr., "Postmaturity", J. Am. Osteopath. Assoc., (Jan. 1976), vol. 75, No. 5, pp. 512-7.
Office Action mailed on Jan. 11, 2008 in U.S. Appl. No. 10/478,262.
Office Action mailed on May 15, 2008 in U.S. Appl. No. 10/478,262.
Office Action mailed on Feb. 19, 2009 in U.S. Appl. No. 10/478,262.
Office Action mailed on Jun. 9, 2009 in U.S. Appl. No. 10/478,262.
Office Action mailed on Nov. 18, 2008 in U.S. Appl. No. 10/478,264.
Office Action mailed on May 22, 2009 in U.S. Appl. No. 10/478,264.
Office Action mailed on Mar. 17, 2008 in U.S. Appl. No. 10/478,357.
Office Action mailed on May 16, 2008 in U.S. Appl. No. 10/478,357.
Office Action mailed on Dec. 16, 2008 in U.S. Appl. No. 10/478,357.
Office Action mailed on May 28, 2009 in U.S. Appl. No. 10/478,357.
Office Action mailed on Apr. 6, 2007 in U.S. Appl. No. 10/478,365.
Office Action mailed on Sep. 7, 2007 in U.S. Appl. No. 10/478,365.
Office Action mailed on Apr. 1, 2008 in U.S. Appl. No. 10/478,365.
Office Action mailed on Jun. 8, 2009 in U.S. Appl. No. 10/478,365.
Office Action mailed on Jan. 24, 2007 in U.S. Appl. No. 10/495,707.
Office Action mailed on Dec. 28, 2007 in U.S. Appl. No. 10/495,707.
Office Action mailed on Aug. 19, 2008 in U.S. Appl. No. 10/495,707.
Office Action mailed on May 22, 2009 in U.S. Appl. No. 10/495,707.
Office Action mailed on Oct. 15, 2007 in U.S. Appl. No. 10/517,509.
Office Action mailed on Dec. 19, 2007 in U.S. Appl. No. 10/517,509.
Office Action mailed on Mar. 26, 2008 in U.S. Appl. No. 10/517,509.
Office Action mailed on Jan. 5, 2009 in U.S. Appl. No. 10/517,509.
Office Action mailed on Aug. 18, 2009 in U.S. Appl. No. 10/517,509.
Office Action mailed on Apr. 3, 2007 in U.S. Appl. No. 10/517,686.
Office Action mailed on Apr. 4, 2008 in U.S. Appl. No. 10/517,686.
Office Action mailed on May 29, 2009 in U.S. Appl. No. 10/517,686.
Visser et al., "In vitro effects of estetrol on receptor binding, drug targets and human liver cell metabolism," Climacteric (2008) 11(1) Appx. II: 1-5.
Visser et al., "First human exposure to exogenous single-dose oral estetrol in early postmenopausal women," Climacteric (2008) 11(1): 1-10.
Visser et al., "Clinical applications of estetrol," J. of Steroid Biochem and Molecular Biol. (2009) 114: 85-89.
Holinka et al., "Estetrol: A unique steroid in human pregnancy," J. of Steroid Biochem and Molecular Biol. (2009) 110: 138-143.
Coelingh Bennink et al., "Oral bioavailability and bone sparing effects of estetrol in an osteoporosis model," Climacteric (2008) 11 (Supp 3): 1-13.
Albertazzi Paola et al., "The Effect of Tibolone Versus Continuous Combined Norethisterone Acetate and Oestradiol on Memory, Libido and Mood of Postmenopausal Women: A Pilot study"; Database Biosis 'Onlinel; Oct. 31, 2000; pp. 223-229; vol. 36, No. 3; Biosciences Information Service, Philadelphia, PA., U.S.
Allen et al., An Ovarian Hormone: Preliminary Report on Its Localization, Extraction and Partial Purification, and Action in Test Animals, JAMA, Sep. 8, 1923, vol. 81, pp. 819-821.
Allen et al., The Induction of a Sexually Mature Condition in Immature Females by Injection of the Ovarian Follicular Hormone, Am. J. Physiol., 1924, vol. 69, pp. 577-588.
Jones et al., The Effects of Various Steroids on the Vaginal Histology in the Rat, Fertility and Sterility, Apr. 1973, vol. 24, No. 4, pp. 284-291.
Tulchinsky et al., Plasma Esterol as an Index of Fetal Well-Being, J. Clin. Endrocrinol. Metab., 1975, vol. 40. pp. 560-567.
Hammond et al., A Versatile Method for the Determination of Serum Cortisol Binding Globulin and Sex Hormone Binding Globulin Binding Capacities, 1983, vol. 132, pp. 101-110.
Elger et al., Sulfamates of Various Estrogens are Prodrugs with Increased Systemic and Reduced Hepatic Estrogenicity at Oral Application, J. Steroid Biochem. Molec. Biol., 1995, vol. 55, No. 3/4, pp. 395-403.

(56) References Cited

OTHER PUBLICATIONS

Murphy et al., Endometrial Effects of Long-Term Low-Dose Administration of RU486, Fertility and Sterility, Apr. 1995, vol. 63, No. 4, pp. 761-766.

Reel et al., Survey and Assessment of Mammalian Estrogen Biological Assays for Hazard Characterization, Fundamental and Applied Toxicology, 1996, vol. 34, pp. 288-305.

Beral et al., Use of HRT and the Subsequent Risk of Cancer, Journal of Epidemiology and Biostatistics, 1999, vol. 4, No. 3, pp. 191-215.

Tavani et al., The Adverse Effects of Hormone Replacement Therapy, Drugs & Aging, May 1999, vol. 14, No. 5, pp. 347-357.

Pike et al., Progestins and Menopause: Epidemiological Studies of Risks of Endometrial and Breast Cancer, Steroids, 2000, vol. 65, pp. 359-664.

Avvakumov et al., Steroid-binding Specificity of Human Sex Hormon-binding Globulin is Influenced by Occupancy of a Zinc-binding Site, The Journal of Biological Chemistry, Aug. 25, 2000, vol. 275, No. 34, pp. 25920-25925.

Holinka, et al., "Comparison of Effects of Esterol and Tamoxifen with Those of Estriol and Estradiol on the Immature Rat Uterus", Biology of Reproduction, Society for the Reproduction Society for the Study of Reproduction, Champaign, IL, US, 1980, vol. 22, No. 4, pp. 913-926.

Jansson et al., "Estrogen Induces a Potent Suppression of Experimental Autoimmune Encephalomyelitis and Collagen-Induced Arthritis in Mice", Journal of Neuroimmunology, Elsevier Science Publishers BV XX, 1994, vol. 53, No. 2, pp. 203-207.

Erdbruegger et al., Drug Discovery Today: Disease Mechanisms (2004), vol. 1, pp. 73-81.

Lab Tests Online (www.labtestsonline.org/understanding/conditions/autoimmune.html) retrieved on Oct. 15, 2009.

www.tiscali.co.uk/lifestyle/healthfitness/health_advice/netdoctor/archive/000489.html, Oct. 15, 2009.

MedlinePlus Medical Encyclopedia: Mutiple Sclerosis, retrieved on Mar. 28, 2008 via www.nlm.nih.gov/medlineplus/ency/article/000737.htm, dated on Aug. 6, 2007, p. 1 and 2; also see WebMD: Multiple Sclerosis—Prevention, retrieved on Mar. 28, 2008 via www.webmd.com/multiple-sclerosis/tc/multiple-sclerosis-ms-prevention, dated on Mar. 23, 2006.

MedlinePlus Medical Encyclopedia: rheumatoid arthritis, retrieved on Mar. 28, 2008 via www.nlm.nih.gov/medlineplus/ency/article/000431.htm, dated on Jul. 27, 2007, p. 1-2 and 4; also WebMD: Rheumatoid Arthritis—Prevention, retrieved on Mar. 28, 2008 via www.webmd.com/rheumatoid-arthritis/tc/rheumatoid-arthritis-prevention, dated on Aug. 23, 2006.

Mueck et al., "Angio and Anti-Angiogenetic Effects of Estradiol and its Metabolites", J. Clin. Basic Cardiol., 2001, pp. 153-155, vol. 4, No. 2.

Shah et al., "Estrogen and Skin. An Overview", Am. J. Clin. Dermatol., 2001, pp. 143-150, vol. 2, No. 3.

Sitruk-Ware et al., "Local Hormonal Treatment for Urogenital Atrophy After Menopause", Shweiz. Rundsch, Med. Praxis, 1997, pp. 1245-1248, vol. 86, No. 33, and Sitruk-Ware, English Translation, 1997. Praxis, Schweizerische Rundschau fur Medizin, vol. 86, No. 33, pp. 1-13.

Schmidt et al., "Treatment of Skin Aging with Topical Estrogens", Int. J. Dermatol., 1996, pp. 669-674, vol. 35, No. 9.

Younglai et al., Journal of Clinical Endocrinology and Metabolism, 1968, vol. 28, Issue 11, pp. 1611-1617.

Webster Ninth New Collegiate Dictionary, 2000, Definition of Prevention, p. 1.

Willhite et al., Pharmacotherapy, 2001, vol. 21, Issue 4, pp. 464-480.

Seeger et al., "The inhibitory effect of endogenous estrogen metabolies on copper-mediated in vitro oxidation of LDL", Int. Journal of Clinical Pharmacology and Therapeutics, (1998), vol. 36, No. 7, pp. 383-385.

Kuipers et al., "Enterohepatic Circulation in the Rat", Gastroenterol., vol. 88, pp. 403-411 (1985).

Schwartz, "A Model for the Regulation of Ovulation in the Rat", Recent Prog. Horm. Res., vol. 25, pp. 1-55, (1969).

Beattie et al., "The Differential Effects of Diestrous Progestogen Administration on Proestrous Gonadotrophin Levels, Endocrinol", vol. 97, pp. 885-890, (1975).

De Visser et al., Endocrinological Studies with (7a, 17 a)-17-Hydroxy-7-me norpregn-5(10)-en-20-yn-3-one (Org OD 14), Arzneim, Forsh., vol. 34, pp. 1010-1020, (1984).

\* cited by examiner

PHARMACEUTICAL COMPOSITION COMPRISING ESTETROL DERIVATIVES FOR USE IN CANCER THERAPY

BACKGROUND OF THE INVENTION

Field of the Invention

The present invention relates to a method for treating or preventing estrogen-sensitive tumours in a mammal by administering an effective amount of a special estrogenic component to said mammal. The method is particularly suited for treating or preventing breast cancer and endometrial cancer.

Breast cancer is one of the leading causes of cancer mortality among Western women, and is predicted to become a leading cause of cancer death in Oriental women in countries such as Japan in the near future. The American Cancer Society estimates that 1 in 9 women face a lifetime risk of this disease, which will prove fatal for about one-quarter of those afflicted with the disease. Breast tumours as well as some other tumours (including uterine cancer, ovarian cancer, endometriosis, uterine fibroids, benign prostatic hyperplasia and melanoma), are known to be estrogen-sensitive, meaning that the formation and growth of such tumours is stimulated by estrogens such as 17β-estradiol. 17β-estradiol is an estrogen that is endogenous to the human body and that is found in both females and males.

Estrogens are known to increase the risk of e.g. breast and endometrial tumours by inducing an estrogen receptor mediated increase in the frequency of breast and endometrial cell division (proliferation). Cell division is essential in the complex process of genesis of human cancer since it per se increases the risk of genetic error, particularly genetic errors such as inactivation of tumour suppressor genes.

An important element of the treatment of estrogen-sensitive tumours, is the suppression or, if possible, elimination of certain estrogen-induced effects. For this purpose, it is desirable to block receptor sites stimulated by estrogens and/or to reduce the amount of estrogen available to act at these sites.

A commonly used therapy to block receptor sites involves the administration of anti-estrogen. Anti-estrogens are a class of chemicals which inhibit estrogens from eliciting their full response in target tissues. An anti-estrogenic compound currently being utilised in the chemotherapy of estrogen-sensitive cancers is tamoxifen. Tamoxifen is a so called selective estrogen receptor modulator (SERM), meaning that the substance exhibits both estrogen antagonist and agonist properties. Although such mixed agonist/antagonists have beneficial effects in the treatment of these cancers, the estrogenic side-effects are also known to have stimulatory effects on certain cancer cell populations in the uterus and therefore, are counterproductive in some cases. SERMs that seem not to display such uterine agonistic effects are also known in the art (e.g. raloxifene), but suffer from the drawback that they can induce climacteric complaints such as hot flushes and sweats. Furthermore, such SERMs have been associated with an enhanced risk of venous thromboembolism, which is another agonistic estrogenic effect.

Reduction of estrogen concentrations in blood serum may be achieved surgically (ovariectomy, adrenalectomy, hypophysectomy) or pharmaceutically through administering high doses of progestogen, GnRH analogue or steroid pathway inhibitors. However, long term suppression of endogenous estrogen production will lead to hypoestrogenism. Furthermore, it is noted that even in the total absence of sex steroids, some receptors may be activated. See Simard and Labrie, "Keoxifene shows pure antiestrogenic activity in pituitary gonadotrophs", Mol. Cell. Endocrinol. 39: 141-144, (1985), especially page 144.

U.S. Pat. No. 4,937,238 (Lemon) relates to a method of preventing breast cancer in female mammals comprising the steps of administering a compound selected from the group of drugs including (1) 4-OH estradiol; (2) d-equilenin; and (3) 17α-ethinyl estriol. A general formula is provided to describe a set of compounds (1) including 4-OH estradiol. Said formula encompasses a huge variety of estrogen-like substances, including substances that may contain 4 or more hydroxyl groups. With the exception of 4-OH estradiol no other representative of this large group of substances are discussed.

U.S. Pat. No. 5,340,584 (Spicer et al.) describes a method for preventing conception or for treating benign gynaecological disorders comprising administering a GnRH composition for a first period of time in an amount effective to suppress ovarian estrogen and progesterone production, simultaneously administering an estrogenic composition in an amount effective to prevent symptoms of estrogen deficiency and simultaneously administering a progestogen in an amount effective to maintain serum level of said progestogen at a level effective to decrease endometrial cell proliferation. The US patent is primarily concerned with slow release formulations that are effective over an extended period of time of at least about two months. In a long list of estrogens that can be used in the claimed invention estetrol is mentioned.

WO 02/30355 (Kragie) describes a method of alleviating adverse side effects and/or enhancing the beneficial efficacy of an aromatase inhibitor in a subject, wherein said method comprises administering a combination of one or more aromatase inhibitors with one or more estrogen function replacement agents (EFR). A wide array of EFR agents are recited in the application, including estrogens. In a list of estrogens also estetrol is mentioned. The claimed method is said to be beneficial for treating subjects suffering from side effects and reduced therapeutic benefit of compositions comprising an aromatase inhibitor administered as a therapeutic for a large variety of disease states or clinical indications. In relation to breast cancer, which is mentioned as an example of a disease state, it is observed that aromatase inhibitors are used to diminish the production of estrogens at the site of cancerous breast tissue. Selective EFR agents such as raloxifene and estradiol metabolites are said to be beneficial as an EFR agent in tumor therapy. As regards estradiol metabolites, reference is made to an article by Lippert T H, et al. Steroids 2000; 65:357-69. Said article reports the results of a study into the effects of A-ring and D-ring metabolites of estradiol, including estetrol, on the proliferation of vascular endothelial cells. The results show that some A-ring metabolites are capable of inhibiting proliferation of cultured endothelial cells of human umbilical cord veins. No significant effect was observed for estetrol.

Estrogen antagonists will usually produce better therapeutic results than therapy which only inhibits estrogen production, e.g. GnRH analogues, aromatase inhibitors and/or progestogens. Consequently, there is a need for a drug that exhibits a more favourable combination of agonistic and antagonistic (or non-agonistic) properties than the anti-estrogens and/or SERMs that are currently available. In particular, there is a need for a drug which does not have undesirable proliferative effects on breast and/or endometrial tissue and which, at the same time, displays sufficient estrogenicity to prevent that its administration will lead to hypoestrogenism and/or climacteric complaints.

SUMMARY OF THE INVENTION

The inventors have unexpectedly found that these requirements are met by estrogenic substances that are represented by the following formula

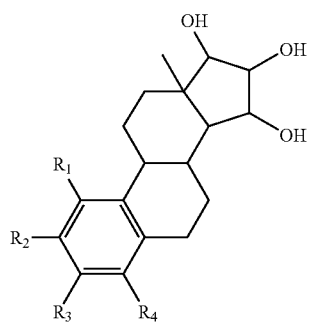

in which formula $R_1, R_2, R_3, R_4$ independently are a hydrogen atom, a hydroxyl group or an alkoxy group with 1-5 carbon atoms.

A known representative of this group of estrogenic substances is 1,3,5 (10)-estratrien-3,15α,16α,17β-tetrol, also known by the names of estetrol, oestetrol and 15α-hydroxyestriol. Estetrol is an estrogen that is produced by the fetal liver during human pregnancy. Unconjugated estetrol levels in maternal plasma peak at about 1.2 ng/ml at term pregnancy and are about 12 times higher in fetal than in maternal plasma (Tulchinsky et al., 1975. J. Clin. Endocrinol. Metab., 40, 560-567).

It is very surprising that the present estrogenic substances can advantageously be used in the treatment of estrogen-sensitive tumours as the skilled person would expect estrogenic substances to enhance the formation and growth of such tumours. Since the present estrogenic substances do not appear to exhibit estrogen antagonistic properties, this finding is truly unexpected.

Although the inventors do not wish to be bound by theory, it is believed that the favourable effect of the present estrogenic component (EC) is caused by a primary mechanism by which said component competes with other estrogens for binding to cytoplasmic estrogen receptors ("ER"). The resulting ER-EC complex is believed to inhibit many of the activities of endogenous estrogen within tumour cells. Endogenous estrogens, such as 17β-estradiol, bind with ERs to promote cellular activities such as estrogen/ER-mediated gene transcription, DNA synthesis, cancer cell growth, and increases in autocrine polypeptides such as transforming growth factor-alpha, epidermal growth factor, insulin-like growth factor-II, and other growth factors that may be involved in cell proliferation. Competitive inhibition of binding of endogenous estrogen to ERs by the present estrogenic component reduces or prevents such cancer growth inducing cellular activities by the endogenous estrogens. Due to the lack of a proliferative impact on e.g. breast tissue, the present estrogenic component prevents the transition of breast cancer cells from the early G1 phase to the mid-G1 phase of the cell cycle and exhibits a cytostatic effect on breast cancer cells.

The present estrogenic substances were found to exhibit a relatively high affinity for the ERα receptor, or conversely a relatively low affinity for the ERβ receptor. It is believed that this receptor specificity is somehow associated with the high efficacy of the present substances in the treatment of estrogen-sensitive tumours. However, the mechanisms that govern the ER signalling pathways that are responsible for this efficacy are as yet poorly understood, despite the considerable scientific effort that is ongoing in this area.

It is known that most estrogens bind to both ERs which, in the presence of tissue-specific co-activators and/or co-repressors, bind to an estrogen response element in the regulatory region of genes or to other transcription factors. Given the complexity of ER signalling, along with the tissue-specific expression of ERα and ERβ and its co-factors, it is now recognised that ER ligands can act as estrogen agonists or even as estrogen antagonists in a tissue-specific manner.

It is also now known that estrogen modulates cellular pharmacology through gene expression, and that the estrogen effect is mediated by the estrogen receptors. The effect of the estrogen receptor on gene regulation can be mediated by a direct binding of ER to the estrogen response element, binding of ER to other transcription factors such as NF-κB, C/EBPβ and through non-genomic effects involving ion channel receptors. Progress over the last few years has shown that ER associates with co-activators (e.g., SRC-1, CBP and SRA) and co-repressors (e.g., SMRT and N—CoR), which also modulate the transcriptional activity of ER in a tissue-specific and ligand-specific manner. In addition, evidence now suggests that the majority of estrogen-regulated genes do not have a classical estrogen response element. In such cases, ER interacts with the transcription factors critical for regulation of these genes. Transcription factors known to be modulated in their activity by ER include, for example, AP-1, NF-κB, C/EBP and Sp-1.

Given the complexity of ER signalling, as well as the various types of tissue that express ER and its co-factors, it is commonly believed that ER ligands can no longer simply be classified as either pure antagonists or agonists. This view is supported by the findings of Paech et al. (Science 277, 1508-1510, 1997) who have reported that 17β-estradiol activates an AP-1 site in the presence of ERα, but inhibits the same site in the presence of ERβ. In contrast, the ER ligands raloxifene (Eli Lilly & Co.) and tamoxifen and ICI-182,780 (Zeneca Pharmaceuticals) stimulate the AP-1 site through ERβ, but inhibit this site in the presence of ERα.

ERα and ERβ are known to have both overlapping and different tissue distributions, as analysed predominantly by RT-PCR or in-situ hybridisation. Very often tissues express both ERα and ERβ, but the receptors are localised in different cell types.

In summary, although the mechanisms by which the present estrogenic component exerts its favourable effect are as yet unknown, it is evident that said estrogenic component is different from estrogenic substances, such as 17β-estradiol and ethinyl estradiol, in that it exhibits a relatively high affinity for the ERα receptor in comparison to the ERβ receptor. It will also be clear from the above that this specificity may well be responsible for the unexpected efficacy of the present estrogenic component in the treatment or prevention of estrogen-sensitive tumours.

Similarly to SERMs like tamoxifen, the present estrogenic component displays estrogenic effects that enable long term administration without the occurrence of climacteric complaints. Tamoxifen, however, has an undesirable estrogenic effect on uterine tissues and has been associated with endometrial hyperplasia and carcinoma. Long term use of tamoxifen is linked to an increased risk of endometrial cancer, up to a fivefold excess of risk relative to women not treated with tamoxifen therapy. Therefore, application of tamoxifen for long term breast cancer prevention and long term treatment of breast cancer has significant associated risks.

Another disadvantage associated with the tamoxifen in premenopausal women is the risk of ovarian hyperstimulation, leading to excessive secretion of estrogen. It will be evident that the resulting increase in estrogen serum level is highly undesirable in patients with estrogen-sensitive tumours. This is why ovariectomy is commonly applied in premenopausal patients that are treated with tamoxifen. The present estrogenic component does not appear to have such an undesirable impact on uterine tissues, nor does it induce ovarian hyperstimulation, because it actually inhibits follicle growth and ovulation.

Another important benefit of the present estrogenic substances is derived from their relative insensitivity to interactions with other drugs (drug-drug interactions). It is well known that certain drugs may decrease the effectiveness of estrogens and other drugs may enhance their activity, resulting in possible increased side-effects. Similarly estrogens may interfere with the metabolism of other drugs. In general, the effect of other drugs on estrogens is due to interference with the absorption, metabolism or excretion of these estrogens, whereas the effect of estrogens on other drugs is due to competition for metabolic pathways.

The clinically most significant group of estrogen-drug interactions occurs with drugs that may induce hepatic microsomal enzymes which may decrease estrogen plasma levels below therapeutic level (for example, anticonvulsant agents; phenytoin, primidone, barbiturates, carbamazepine, ethosuximide, and methosuximide; antituberculous drugs such as rifampin; antifungal drugs such as griseofulvin). The present estrogenic substances are less dependent on up- and downregulation of microsomal liver enzymes (e.g. P450's) and also are less sensitive to competition with other P450 substrates. Similarly, they do not interfere significantly in the metabolism of other drugs.

The conjugates of most estrogens, as formed in the liver, are excreted in the bile and may be broken down by gut bacteria in the colon to liberate the active hormone which can then be reabsorbed (enterohepatic recirculation). There are clinical reports that support the view that enterohepatic recirculation of estrogens decreases in women taking antibiotics such as ampicillin, tetracycline, etc. Conjugated forms of the present estrogenic substances are hardly excreted in the bile, meaning that they are substantially insensitive to drugs that do influence the enterohepatic recirculation of other estrogens.

The above observations serve to explain why the estrogenic substances of the invention are particularly suitable for treating or preventing estrogen-sensitive tumours.

DETAILED DESCRIPTION OF THE INVENTION

Figure 1:
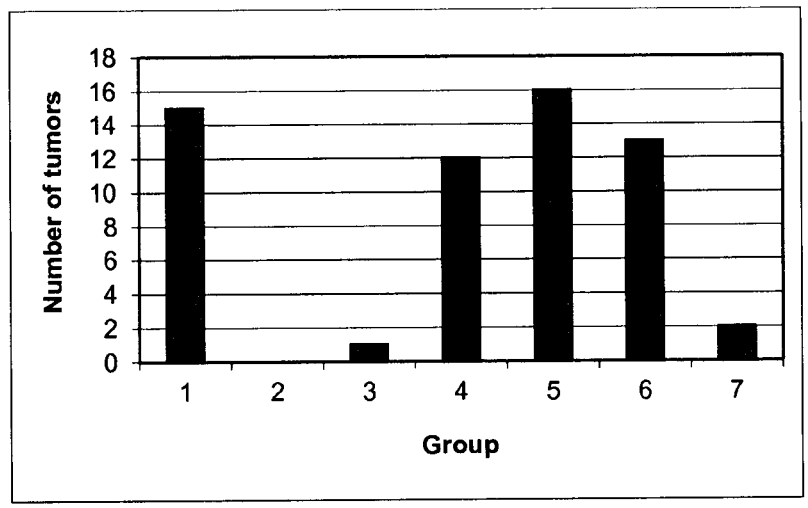
FIG. 1 shows the number of mammary tumours per the following treatment groups (n=12): Group 1 oral treatment with 3.0 ml/kg/day vehicle; Group 2 surgically castrated animals receiving placebo treatment with 3.0 ml/kg/day vehicle; Group 3 tamoxifen 3 mg/kg/day orally; Group 4 ethinylestradiol (EE) 0.025 mg/kg/day orally; Group 5 EE 0.125 mg/kg/day orally; Group 6 estetrol (E4) 0.5 mg/kg/day orally; Group 7 E4 2.5 mg/kg/day orally.

Accordingly, the present invention relates to a method of treating or preventing estrogen-sensitive tumours in a mammal, said method comprising the administration of a therapeutically effective amount of an estrogenic component to said mammal, wherein the estrogenic component is selected from the group consisting of:

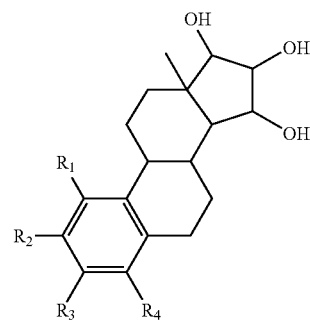

substances represented by the following formula in which formula $R_1$, $R_2$, $R_3$, $R_4$ independently are a hydrogen atom, a hydroxyl group or an alkoxy group with 1-5 carbon atoms; precursors capable of liberating a substance according to the aforementioned formula when used in the present method; and mixtures of one or more of the aforementioned substances and/or precursors.

As used herein the term "tumour" refers to a new growth of tissue in which the multiplication of cells is uncontrolled and progressive. The term tumour encompasses both malignant and benign tumours.

The term "estrogen-sensitive tumour" refers to a tumour whose formation and growth is stimulated by estrogens, other than the estrogenic components according to the present invention, especially estrogens selected from the group consisting of 17β-estradiol, ethinyl estradiol, as well as precursors and metabolites thereof.

The term "cancer" refers to cells that have undergone a malignant transformation that makes them pathological to the host organism.

The present estrogen substances are distinct from both the biogenic and synthetic estrogens that are commonly applied in pharmaceutical formulations in that the 5 membered ring in the steroid skeleton comprises 3 hydroxyl substituents rather than 0-2. In a particularly preferred embodiment at least one of $R_1$, $R_2$, $R_3$ and $R_4$ represents a hydroxyl group, meaning that the estrogen substance contains at least 4 hydroxyl groups. Preferably, the estrogenic component applied as the active component in the present composition is a so called biogenic estrogen, i.e. an estrogen that occurs naturally in the human body, a precursor of a biogenic estrogen or a mixture thereof. Because biogenic estrogens are naturally present in the fetal and female body, side-effects are not expected to occur, particularly not if the serum levels resulting from the exogenous administration of such estrogens do not substantially exceed naturally occurring concentrations.

In a preferred embodiment of the present invention the estrogenic substance contains 4 hydroxyl groups. In another preferred embodiment, no more than 3 of $R_1$, $R_2$, $R_3$, $R_4$ are hydrogen atoms. Also, in the aforementioned formula, $R_1$ preferably represents a hydrogen atom. In said formula preferably at least 2, more preferably at least 3 of the groups $R_1$, $R_2$, $R_3$ and $R_4$ represent a hydrogen atom.

The estrogenic substances according to the formula encompass various enantiomers since the carbon atoms that carry hydroxyl-substituents are chirally active. In one preferred embodiment, the present estrogenic substance is 15α-hydroxy substituted. In another preferred embodiment the substance is 16α-hydroxy substituted. In yet another preferred embodiment, the substance is 17β-hydroxy substituted. Most preferably the estrogenic substances are 15α,16α,17β-trihydroxy substituted. The other chirally active carbon atoms in the steroid skeleton of the present estrogenic components preferably have the same configuration as the corresponding carbon atoms in 17β-estradiol and other biogenic estrogens.

In a preferred embodiment of the present invention $R_3$ represents a hydroxyl group or an alkoxy group. In another preferred embodiment the groups $R_1$, $R_2$ and $R_4$ represent hydrogen atoms, in which case the substance is 1,3,5 (10)-estratrien-3,15,16,17-tetrol. A preferred isomer of the latter substance is 1,3,5 (10)-estratrien-3,15α,16α,17β-tetrol (estetrol).

The invention also encompasses the use of precursors of the estrogen substances that constitute the active component in the present method. These precursors are capable of liberating the aforementioned estrogen substances when used in the present method, e.g. as a result of metabolic conversion. These precursors are preferably selected from the group of derivatives of the present estrogen substances, wherein the hydrogen atom of at least one of the hydroxyl groups has been substituted by an acyl radical of a hydrocarbon carboxylic, sulfonic acid or sulfamic acid of 1-25 carbon atoms; tetrahydrofuranyl; tetrahydropyranyl; or a straight or branched chain glycosydic residue containing 1-20 glycosidic units per residue. Typical examples of precursors which can suitably be used in accordance with the invention are esters that can be obtained by reacting the hydroxyl groups of the estrogen substances with substances that contain one or more carboxy ($M^+\ {}^-OOC—$) groups, wherein $M^+$ represents a hydrogen or (akali)metal cation. Hence, in a particularly preferred embodiment, the precursors are derivatives of the estrogen substances, wherein the hydrogen atom of at least one of the hydroxyl groups in said formula has been substituted by —CO—R, wherein R is a hydrocarbon radical comprising from 1-25 carbon atoms. Preferably R is hydrogen, or an alkyl, alkenyl or aryl radical comprising from 1-20 carbon atoms.

The method according to the present invention may suitably be used to treat mammals such as cattle, pets and particularly humans. The method may be used to treat both females and males (e.g. prostatic hyperplasia), be it that best results are obtained in females. The method may be applied advantageously in premenopausal, perimenopausal and postmenopausal females. Since the present method, unlike SERMs such as tamoxifen, is not associated with the risk of ovarian hyperstimulation, it is especially suited for the treatment of pre- and perimenopausal females. The present method may advantageously be used to treat estrogen sensitive tumours and also to prevent the occurrence of such tumours.

The present method is particularly effective when the administration is continued for a prolonged period of time. Usually, the method comprises the uninterrupted administration of the estrogenic component during a period of at least 5 days. Preferably the uninterrupted administration is continued for at least 30 days, more preferably for at least 90 days.

The present method may suitably employ enteral or parenteral administration of the estrogenic component. The term "parenteral administration" as used in here encompasses transdermal, intravenous, intranasal, intravaginal, pulmonary, buccal, subcutaneous, intramuscular and intra-uterine administration. The term "enteral administration" includes oral as well as rectal administration.

Preferably the mode of administration is selected from the group consisting of oral, transdermal, intravenous, intranasal, intravaginal, pulmonary, rectal, buccal, subcutaneous, intramuscular or intra-uterine administration. More preferably the mode of administration is selected from the group consisting of oral, transdermal, intravenous, subcutaneous, intranasal, pulmonary and vaginal administration. In a particularly preferred embodiment the present method employs oral, transdermal, intranasal or subcutaneous administration. Even more preferably the present method employs oral or transdermal administration.

Oral, intravenous, subcutaneous, intramuscular, intranasal, rectal, buccal and pulmonary administration are ideally suited for (at least) once daily administration. Transdermal administration is advantageously applied at frequencies between once a day and once a month. Intravaginal and intra-uterine administrations are advantageously operated at administration frequencies between once weekly and once monthly. Subcutaneous and intramuscular administration may also suitably be done in the form of depot injections at intervals of 1 week to 6 months, preferably at intervals of 4 weeks to 3 months.

For reasons of convenience, the present method preferably utilises administration intervals of 1 day, 1 week or 1 month. Regimens that employ once daily oral, subcutaneous, intravenous or intranasal administration, once weekly transdermal or once monthly intravaginal or subcutaneous administration are particularly preferred.

Although the present method may employ slow release formulations such as the ones described in U.S. Pat. No. 5,340,584, it is preferred not to employ slow release formulations that are effective over an extended period of at least about one month.

Irrespective of the mode of administration, the estrogenic component is preferably administered in an amount effective to achieve a blood serum concentration of at least 1 nanogram per liter, more preferably of at least 10 nanogram per liter, most preferably at least 100 nanogram per liter. Generally the resulting blood serum concentration of the estrogenic component will not exceed 100 μg per liter, preferably it will not exceed 50 μg per liter, more preferably it will not exceed 25 μg per liter.

In a particularly preferred embodiment, the estrogenic component is administered in an amount that clearly exceeds the amount required to maintain serum level of said estrogenic component at a level effective to prevent symptoms of estrogen deficiency, as taught by U.S. Pat. No. 5,340,584. Even more preferably the estrogenic component is administered in an amount sufficient to maintain serum level of said estrogenic component at a level equivalent to a serum level of estradiol of more than 50 pg/ml, most preferably of more than 140 pg/ml.

In accordance with the present method the estrogenic component is usually administered in an amount of less than 1 mg per kg of bodyweight per day, preferably of less than 0.4 mg per kg of bodyweight per day. In order to achieve a significant impact from the administration of the estrogenic component, it is advisable to administer in an amount of at least 1 μg per kg of bodyweight per day. Preferably, the administered amount is at least 5 μg per kg of bodyweight per day.

Oral administration of the active component is preferably done in an amount of less than 400 μg per kg of bodyweight per day, preferably of less than 200 μg per kg of bodyweight per day. In order to achieve a significant impact from the administration of the active component, it is advisable to orally administer in an amount of at least 2 μg per kg of bodyweight per day. Preferably, the orally administered amount is at least 5 μg per kg of bodyweight per day. In the present method, particularly when used in humans, the estrogenic component is usually administered in an average dosage of at least 0.05 mg per day, preferably of at least 0.1 mg per day. The maximum dosage is normally kept below 40 mg per day, preferably below 20 mg per day.

The present method of treatment comprises administering to a mammal in need of such a therapy an effective amount of the estrogenic component. The amount needed to be effective will differ from individual to individual and are determined by factors such as the individual's gender, body weight, route of administration and the efficacy of the particular estrogenic component used.

In the present method, particularly when used in humans, the estrogenic component is usually administered orally in an average dosage of between 0.01 and 20 mg per day, preferably of between 0.05 and 10 mg per day. Similarly, the parenteral dosage preferably is at least 0.05, preferably at least 0.1 mg per day. The average maximum parenteral dosage is normally kept below 40 mg per day, preferably below 20 mg per day.

In a particularly preferred embodiment of the invention the method employs oral administration of the active estrogenic component. The term oral administration as used in here also encompasses oral gavage administration. The inventors have found that, despite its low potency, estrol and related estrogenic substances may advantageously be administered orally. Although the inventors do not wish to be bound by theory, it is believed that the efficacy of orally administered estetrol-like substances results from the combination of special pharmacokinetic (ADME) and pharmacodynamic properties of these substances.

The inventors have discovered that the oral bioavailability of estetrol-like substances is exceptionally high and that their in vivo half-life is considerably longer than that of commonly used biogenic estrogens. Thus, even though estetrol and estetrol-like substances have relatively low estrogenic potency, they may effectively be administered orally because the oral dosages required to achieve the desired effect are similar to those already used for e.g. 17β-estradiol.

Another important advantage of oral administration of estetrol and estetrol-like substances resides in the fact that the hepatic effects of these substances are deemed to be minimal since they are hardly metabolised during the so called "first pass". The first-pass effect of drugs given orally refers to the process of drug degradation by the liver during a drug's transition from initial ingestion to circulation in the blood stream. After resorption from the intestinal lumen, orally applied active ingredients enter the organism via the liver. This fact is of specific importance for estrogenic agents as the liver is a target organ for estrogens; oral intake of estrogens results in strong estrogenic effects in the liver. Therapeutically equivalent doses of commonly used biogenic estrogens, when applied orally, result in clear responses of hepatic parameters, such as increase of SHBG, CBG and angiotensinogen. These hepatic effects of estrogens are also observed when equine estrogen formulations (so-called conjugated estrogens) are used.

The present method may suitably be used in the (prophylactic) treatment of various estrogen-sensitive tumours, including breast cancer, uterine cancer, ovarian cancer, endometriosis, uterine fibroids, benign prostatic hyperplasia and melanoma. The term "uterine cancer" encompasses endometrial cancer and cervix cancer. The present is method is deemed to be particularly suitable for treating or preventing breast cancer and endometrial cancer. The method of the present invention is most advantageously employed in treating or preventing breast cancer.

In order to further enhance the effectiveness of the present method it may be advisable to co-administer a pharmaceutical component that is capable of suppressing blood serum levels of endogenous estrogens. Preferably one or more of such estrogen suppressants are co-administered in an effective amount to suppress blood serum 17β-estradiol level to below 10 pg/ml, more preferably to below 5 pg/ml, most preferably to below 1 pg/ml.

Examples of estrogen suppressants that may advantageously be co-administered together with the present estrogenic component include progestogens, GnRH analogues, aromatase inhibitors, cyclo-oxygenase 2 (COX-2) inhibitors and 17β-hydroxysteroid dehydrogenase type 1 (17β-HSD type 1) inhibitors. Preferably, the present method comprises the co-administration of an estrogen suppressant selected from the aforementioned group of enzyme inhibitors. These enzyme inhibitors offer the advantage that they enable the selective to suppression of endogenous estrogen production without directly affecting the production of other steroids and/or gonadotrophins.

In principle, GnRH compositions, as described in U.S. Pat. No. 5,340,584 and U.S. Pat. No. 5,340,585, may also be employed as estrogen suppressants in the present method. Preferably, however, the present method does not employ such a GnRH composition, particularly not if the present method is employed to prevent the occurrence of estrogen-sensitive tumours.

Enzyme inhibitors such as aromatase inhibitors, COX-2 inhibitors and 17β-HSD type 1 inhibitors are capable of blocking biosynthetic pathways that are involved in the endogenous production of the most important endogenous estrogen, i.e. 17β-estradiol. These pathways may be represented as follows:

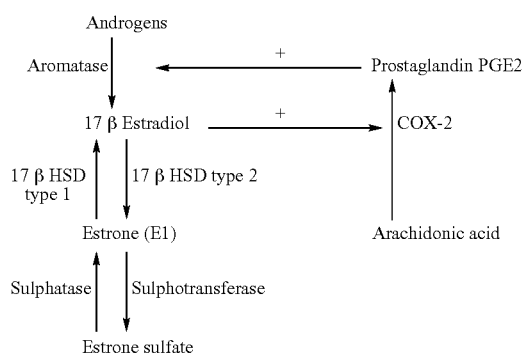

As is evident from the above diagram, aromatase and 17β-hydroxysteroid dehydrogenase type 1 are key enzymes in the endogenous production of 17β-estradiol. Consequently, the inhibition of aromatase and 17β-hydroxysteroid dehydrogenase type 1 will automatically reduce the endogenous production of 17β-estradiol, which in turn will impair estrogen-induced proliferation.

The diagram also shows that prostaglandin PGE2 is capable of stimulating aromatase activity. Consequently, inhibition of cyclo-oxygenase 2 (COX-2), the enzyme responsible for the endogenous production of PGE2 from arachidonic acid, will automatically cause a reduction of aromatase activity and a corresponding decrease in estrogen-induced proliferation.

Thus it may be concluded that aromatase inhibitors, cyclo-oxygenase 2 (COX-2) inhibitors as well as 17β-hydroxysteroid dehydrogenase type 1 inhibitors may suitably be used to impair endogenous production of estrogens, particularly the endogenous production of 17β-estradiol.

Aromatase is one of the P-450 enzymes. It catalyses the aromatisation of the A ring of the steroid skeleton in the steroid biosynthetic pathway starting from the cleavage of the side chain of cholesterol. To be more precise: aromatase catalyses the conversion of androstenedione to estrone as well as the conversion of testosterone to estradiol. Hence aromatase is a rate limiting enzyme for the biosynthesis of the latter estrogens.

Aromatase inhibitors are substances capable of inhibiting the catalytic activity of aromatase. In the context of the present invention aromatase inhibitors are substances that may be administered to animals, and especially humans, in non-toxic dosages so as to inhibit estrogen biosynthesis. At present a range of aromatase inhibitors is available and includes substances such as aminoglutethimide, anastrozole, exemestane, vorozole, letrozole, fadrozole, rogletimide, atamestane, formestane, liarozole, YM 511, TZA-2237, CGS 16949A and MEN 11066. Aromatase inhibitors primarily find application in methods of treating breast cancer. It has also been suggested that aromatase inhibitors may be used in the treatment of endometriosis. Takayama et al. (Fertility Sterility 1998; 69(4); 709-13) successfully treated one case of an unusually aggressive recurrent postmenopausal endometriosis with an aromatase inhibitor. All existing therapies with aromatase inhibitors are based on oral or intramuscular administration.

Cyclooxygenase (COX), also known as prostaglandin G/H synthase, is a membrane-bound enzyme, responsible for the oxidation of arachidonic acid to prostaglandins, that was first identified over 20 years ago. In the past decade, however, more progress has been made in understanding the role of cyclo-oxygenase enzymes in various pathophysiological conditions. Two cyclo-oxygenase isoforms have been identified and are referred to as COX-1 and COX-2. COX-1 enzyme is constitutively expressed and regulates a number of housekeeping functions such as vascular haemostasis and gastro-protection, whereas COX-2 is inducible (i.e., sites of inflammation) by a number of mediators such as growth factors, cytokines and endotoxins.

Examples of 17β-hydroxysteroid dehydrogenase type 1 inhibitors (17β-HSD type 1 inhibitors) include: N-butyl, N-methyl, 9-[3'17'beta-(dihydroxy)-1',3',5'(10')-estratien-16 alpha-yl]-7 bromononamide; N-butyl, N-methyl, 7-[3', 17'beta-dihydroxy-1',3',5'(10')-estratiene-6' beta-yl]-7-thia-heptanamide.

In a preferred embodiment, the present method comprises the co-administration of an to aromatase inhibitor in an effective amount to suppress endogenous estrogen production. Aromatase inhibitors can suitably be used to achieve a very significant reduction in endogenous estrogen production without serious side-effects. An important side-effect normally associated with aromatase inhibitors, as well as with other suppressants of endogenous estrogen production, i.e. hypoestrogenism, is effectively neutralised by the co-administration of the present estrogenic component.

In a particularly preferred embodiment, the present method comprises the co-administration of a progestogen in an effective amount to suppress endogenous estrogen production. The co-administration of progestogen offers the additional advantage that progestogens are known to inhibit the proliferative effect of estrogens on the endometrium. Although the present estrogenic components, unlike certain SERMs, do not appear to have a pronounced proliferative effect on the endometrium, the co-administration of progestogen may be advisable to rule out any potential risks.

Examples of progestogens which may suitably be used in accordance with the present invention include: progesterone, levonorgestrel, norgestimate, norethisterone, dydrogesterone, drospirenone, 3-beta-hydroxydesogestrel, 3-keto desogestrel (=etonogestrel), 17-deacetyl norgestimate, 19-norprogesterone, acetoxypregnenolone, allylestrenol, anagestone, chlormadinone, cyproterone, demegestone, desogestrel, dienogest, dihydrogesterone, dimethisterone, ethisterone, ethynodiol diacetate, flurogestone acetate, gastrinon, gestodene, gestrinone, hydroxymethylprogesterone, hydroxyprogesterone, lynestrenol (=lynoestrenol), medrogestone, medroxyprogesterone, megestrol, melengestrol, nomegestrol, norethindrone (=norethisterone), norethynodrel, norgestrel (includes d-norgestrel and dl-norgestrel), norgestrienone, normethisterone, progesterone, quingestanol, (17alpha)-17-hydroxy-11-methylene-19-nor-pregna-4,15-diene-20-yn-3-one, tibolone, trimegestone, algestone acetophenide, nestorone, promegestone, 17-hydroxyprogesterone esters, 19-nor-17hydroxyprogesterone, 17alpha-ethinyl-testosterone, 17alpha-ethinyl-19-nor-testosterone, d-17beta-acetoxy-13beta-ethyl-17alpha-ethinyl-gon-4-en-3-one oxime and precursors of these compounds that are capable of liberating these progestogens in vivo when used in the present method. Preferably the progestogen used in the present method is selected from the group consisting of progesterone, desogestrel, etonogestrel, gestodene, dienogest, levonorgestrel, norgestimate, norethisterone, drospirenone, trimegestone, dydrogesterone, precursors of these progestogens and mixtures thereof.

Another aspect of the invention concerns a pharmaceutical composition containing: at least 0.01 mg of an estrogen suppressant selected from the group consisting of aromatase inhibitors, GnRH analogues cyclo-oxygenase 2 (COX-2) inhibitors, 17β-hydroxysteroid dehydrogenase (HSD) type 1 inhibitors and combinations thereof; at least 0.05 mg of the estrogenic component as defined herein before; and pharmaceutically acceptable excipient. In a preferred embodiment, the estrogen suppressant is selected from the group consisting of aromatase inhibitors, COX-2 inhibitors, 17β-HSD type 1 inhibitors and combinations thereof. Most preferably the estrogen suppressant is an aromatase inhibitor.

In a particularly preferred embodiment, the pharmaceutical composition according to invention contains aromatase inhibitor in an amount equivalent to an oral dosage of at least 0.05 mg anastrozole.

The present invention also encompasses a drug delivery system comprising a pharmaceutical composition as defined above, said drug delivery system being selected from the group consisting of an oral dosage unit; an injectable fluid; a suppository; a pessary; a gel; and a cream. In a particularly preferred embodiment said drug delivery system is selected from the group consisting of an oral dosage unit, a suppository, a pessary, a gel and a cream. Most preferably, the drug delivery system is an oral dosage unit.

Yet another aspect of the invention relates to a pharmaceutical kit comprising one or more dosage units containing at least 0.05 mg of the present estrogenic component and a pharmaceutically acceptable excipient; and one or more dosage units containing at least 0.01 mg of an estrogen suppressant selected from the group consisting of GnRH analogues, aromatase inhibitors, cyclo-oxygenase 2 (COX-2) inhibitors, 17β-hydroxysteroid dehydrogenase type 1 inhibitors and combinations thereof, and a pharmaceutically acceptable excipient. Preferably, the dosage units contain the estrogen component in combination with one or more of the aforementioned enzyme inhibitors.

The estrogenic component and the estrogen suppressant can be incorporated in the present kit in the form of separate dosage units. However, it is also possible and indeed very convenient to combine these two components into a single dosage unit.

The pharmaceutical kit preferably contains dosage units for oral, transdermal, intravenous, intranasal, intravaginal, pulmonary, rectal, buccal, subcutaneous, intramuscular and/or intra-uterine administration. More preferably the dosage units are designed for oral, transdermal, intravenous, subcutaneous, intranasal, pulmonary and/or vaginal administration. In a particularly preferred embodiment the kit comprises dosage units for oral, transdermal, intranasal and/or subcutaneous administration. Most preferably, the dosage units are oral to dosage units.

The present estrogenic component can suitably be administered in any form of pharmaceutical formulation known in the art. The pharmaceutical formulation can be a solid or semi-solid dosage form such as tablets, capsules, cachets, pellets, pills, powders and granules, as well as fluid dosage forms such as solutions, emulsions, suspensions, ointments, pastes, creams, gels, jellies and foams.

Examples of oral dosage units that may be used in the present method include solid or semi-solid dosage forms such as tablets, capsules, cachets, pellets, pills, powders and granules. The term "solid or semi-solid dosage form" also encompasses capsules that contain a liquid, e.g. an oil, in which the present estrogenic component is dissolved or dispersed. Tablets and equivalent solid and semi-solid dosage forms can suitably contain materials such as binders (e.g. hydroxypropylmethyl cellulose, polyvinyl pyrrolidine, other cellulosic materials and starch), diluents (e.g. lactose and other sugars, starch, dicalcium phosphate and cellulosic materials), disintegrating agents (e.g. starch polymers and cellulosic materials) and lubricating agents (e.g., stearates and talc).

Suitable transdermal delivery systems include patches, gels, tapes and creams, and can contain excipients such as solubilisers, permeation enhancers (e.g. fatty acids, fatty acid esters, fatty alcohols and amino acids), hydrophilic polymers (e.g. polycarbophil and polyvinyl pyrrolidine) and adhesives and tackifiers (e.g. polyisobutylenes, silicone-based adhesives, acrylates and polybutene).

Examples of transmucosal (notably rectal and intravaginal) delivery systems include patches, tablets, suppositories, pessaries, gels, and creams, and can contain excipients such as solubilizers and enhancers (e.g. propylene glycol, bile salts and amino acids), and other vehicles (e.g. polyethylene glycol, fatty acid esters and derivatives, and hydrophilic polymers such as hydroxypropylmethyl cellulose and hyaluronic acid).

Injectable or implantable depot preparations may take the form of injectable fluids and implantation tablets. Suitable fluid carrier components are physiologically compatible diluents wherein the active agents can be dissolved, suspended. An example of a diluent is water, with or without addition of electrolyte salts or thickeners. Thus, the depot formulation can be, for example, an aqueous microcrystalline suspension. Oils are particularly suitable as diluents, with or without the addition of a solubiliser, of a surfactant, or of a suspension or emulsifying agent. Examples of suitable oils include arachidis oil, olive oil, peanut oil, cottonseed oil, soybean oil, castor oil, and sesame oil. Examples of solubilisers include benzyl alcohol and benzyl benzoate. Depot preparations offer the advantage that a single injection or implantation suffices for one or several months. Duration of the depot effect depends the nature of the estrogenic component (the ester precursors being preferred as they display a slower release), the amount of the estrogenic component as well as on the type of carrier substance that releases the active agent. Generally, the duration will be in the range of 10-30 days, but longer or shorter times can also be achieved.

Other delivery systems that can be used for administering the estrogenic components of the invention include intranasal and pulmonary delivery systems such as sprays and microparticles.

The invention is further illustrated by the following examples:

EXAMPLES

Example 1

Established competitive steroid binding assays were used to determine the relative binding affinity of estetrol (E4), as compared to 17α-ethinylestradiol (EE) and 17β-estradiol (E2), to human Estrogen Receptor (ER) α- and β-forms.

The method employed was adapted from the scientific literature and described in detail by Osbourn et al. (1993, Biochemistry, 32, 6229-6236). Recombinant human ERα and ERR proteins were purified from transfected Sf9-cells. The in vitro assays involved the use of either ERα or ERβ proteins and [$^3$H]E2, at a fixed concentration of 0.5 nM, as the labeled ligand. Recombinant human ERα or ERβ proteins were dissolved in binding buffer (10 mM Tris-HCL, pH 7.5, 10% glycerol, 1 mM DTT, 1 mg/ml BSA) and duplicate aliquots were then incubated with [$^3$H]E2 at a final concentration of 0.5 nM, together with a vehicle control (0.4% DMSO), or the same amount of vehicle containing increasing concentrations of unlabeled steroid ligands as competitors. After incubation for 2 h at 25° C., the unbound ligands were removed and the amounts of [$^3$H]E2 bound to either ERα or ERβ proteins were measured. The average amounts of [$^3$H]E2 bound to either ERα or ERβ proteins at each concentration of competitor were used to make inhibition curves. IC50 values were subsequently determined by a non-linear, least squares regression analysis. Inhibition constants (Ki) were calculated using the equation of Cheng and Prusoff (Cheng et al., 1973, Biochem. Pharmacol., 22, 3099-3108), using the measured IC50 of the tested compounds, the concentration of radioligand employed in the assay, and the historical values for the Kd of the radioligand, which were established as 0.2 nM and 0.13 nM for ERα and ERβ, respectively. Biochemical assay results for E4 are presented as the percent inhibition of specific binding in three separate experiments (Table 1). For comparison of binding affinities of E4, EE and E2 to human ERα and ERβ proteins, experimentally observed Ki values are shown in Table 2. As compared to EE and E2, E4 demonstrates a unique binding profile with a strong preference (400%) for binding to the ERα protein (Table 2). In contrast, Ki values for ERβ protein are more pronounced for EE and E2 steroid ligands (Table 2).

TABLE 1

Percent inhibition of specific binding to ERα and ERβ proteins using E4 as unlabeled steroid ligand and 0.5 nM [3H] E2 as labeled competitor. Results of three separate experiments are shown.

| E4 final concentration | Percent inhibition of specific binding in | | | | | |
|---|---|---|---|---|---|---|
| | ERα steroid binding assay | | | ERβ steroid binding assay | | |
| | Test 1 | Test 2 | Test 3 | Test 1 | Test 2 | Test 3 |
| 1 µM | 98 | nd | Nd | 87 | 90 | 95 |
| 0.3 µM | 92 | 94 | 101 | 74 | 74 | 77 |
| 0.1 µM | 83 | 85 | 86 | 56 | 54 | 50 |
| 0.03 µM | 64 | 66 | 63 | 19 | 25 | 30 |
| 10 nM | 43 | 32 | 28 | nd | nd | nd |
| 3 nM | 26 | 17 | 11 | nd | nd | nd | nd: not determined

TABLE 2

Experimentally determined inhibition constants (Ki) for estetrol (E4), 17α-ethinylestradiol (EE) and 17β-estradiol (E2), to human ERα and ERβ proteins. Relative preference for binding to ERα protein is also shown.

| Steroid ligands | Ki ERα (nM) | Ki ERβ (nM) | Relative ERα/ERβ preference(%) |
|---|---|---|---|
| EE | 0.23 | 0.025 | 11 |
| E2 | 0.21 | 0.015 | 7 |
| E4 | 4.9 | 19 | 400 |

Example 2

To determine the bioavailability and elimination half-life of estetrol after oral dosing in humans a single rising dosing study was performed in healthy postmenopausal volunteers. Volunteers (n=6) were randomly assigned to 0.1, 1 or 10 mg estetrol and blood samples (18 per volunteer) were obtained over a period of 72 hours.

After thawing the plasma samples, liquid-liquid extraction (hexane and diethyl ether) was employed to prepare the estetrol-containing plasma samples for HPLC analysis (Perkin is Elmer 200) and tandem mass spectrometry using a PE Sciex 4000 tandem mass spectrometer and APCI interface. With each sample batch, a calibration curve with 6 calibrators was recorded. The calibration curve was calculated using linear regression (correlation coefficient>0.98), which permitted quantitation of plasma concentrations.

Good tolerability was observed when increasing the oral estetrol dose from 0.1 to 1 and further to 10 mg. AUC values demonstrated good dose-linearity, indicating that, over the entire dose range, orally administered estetrol was well absorbed. Interestingly, estetrol demonstrated a long elimination half-life of more than 20 hours, i.e. 20-50 hours in human postmenopausal subjects.

Example 3

In order to assess the anti-tumour efficacy of the estrogenic substances of the present invention, estetrol was tested in the 7,12-dimethyl-benz(a)anthracene (DMBA)-induced tumour model in rats. This model, originally developed by Huggins et al., 1961 (Nature, 19, 204-207), has been widely used and is a generally accepted model with predictive value for anti-tumour agents in humans. The growth of the DMBA-induced tumours is dependent on endogenously produced estradiol or exogenously administered estrogens and prolactin (Sylvester et al., 1982, Cancer Research, 42, 4943-4947). Ovariectomy (Hollingsworth et al., 1998, Breast Cancer Research and Treatment, 47, 63-70), androgens (Dauvois et al., 1989, Breast Cancer Treatment, 14, 299-306), tamoxifen (Hollingsworth et al., 1998, Breast Cancer Research and Treatment, 47, 63-70), progestogens (Kelly et al. 1979, Eur. J. Cancer, 15, 1243-1251; Russo et al., 1987, Lab. Invest. 57, 112-137) and GnRH analogues (Hollingsworth et al., 1998, Breast Cancer Research and Treatment, 47, 63-70) all have been shown to be effective anti-tumour treatments in the DMBA model.

Eighty-four female Sprague-Dawley rats (Harlan, The Netherlands) were group housed, maintained in a 12-hr light/dark environment, and fed a Soya Free Diet (SDS England) and water ad libitum. Animals were weighed on a weekly basis. One week prior to induction of mammary carcinoma, 12 animals (aged 43 days) were surgically castrated via removal of the ovaries. At the age of 50 days, all animals were administered a single oral dose of 16 mg DMBA to induce tumour development. Animals were subsequently allocated to one of seven groups (n=12), receiving placebo or treatment as follows:

Group 1 animals received placebo oral treatment with 3.0 ml/kg/day vehicle (20% wt/vol solution of hydroxypropyl-beta-cyclodextrin in water);

Group 2 surgically castrated animals received placebo treatment with 3.0 ml/kg/day vehicle;

Group 3 animals received the anti-estrogen tamoxifen given orally at a single daily dose of 3 mg/kg;

Group 4 animals received ethinylestradiol (EE) orally at a single daily dose of 0.025 mg/kg;

Group 5 animals received ethinylestradiol (EE) orally at a single daily dose of 0.125 mg/kg;

Group 6 animals received estetrol (E4) orally at a single daily dose of 0.5 mg/kg; and Group 7 animals received estetrol (E4) orally at a single daily dose of 2.5 mg/kg. The doses of EE and E4 were based on data from previous studies, showing equipotency of 0.025 mg/kg/day EE and 0.5 mg/kg/day E4 in agonistic models of preventing bone resorption, prevention of hot flushing and vaginal cornification. Similarly, the doses of 0.125 mg/kg/day EE and 2.5 mg/kg/day E4 showed equipotency in in vivo estrogenicity in preventing bone resorption, prevention of hot flushing and vaginal cornification.

During the treatment period of 8 weeks, the emergence of palpable tumours and number of tumours were determined weekly. At 8 weeks, at necropsy, final measurements were taken. The number of tumours at necropsy are depicted in FIG. 1.

As is clearly demonstrated by the absence of tumours in the ovariectomized animals (group 2), development of DMBA-induced mammary tumours is estrogen-dependent. As expected, also tamoxifen showed anti-tumour properties by inhibiting the development of mammary tumours in this model. Surprisingly, and in contrast to the effect seen with the 0.125 mg/kg/day dose of EE, E4 at an equipotent agonistic dose of 2.5 mg/kg/day markedly suppressed mammary tumour development. Furthermore, this particular dose of E4 was as effective as tamoxifen in preventing growth of DMBA-induced tumours.

Example 4

Figure 2:
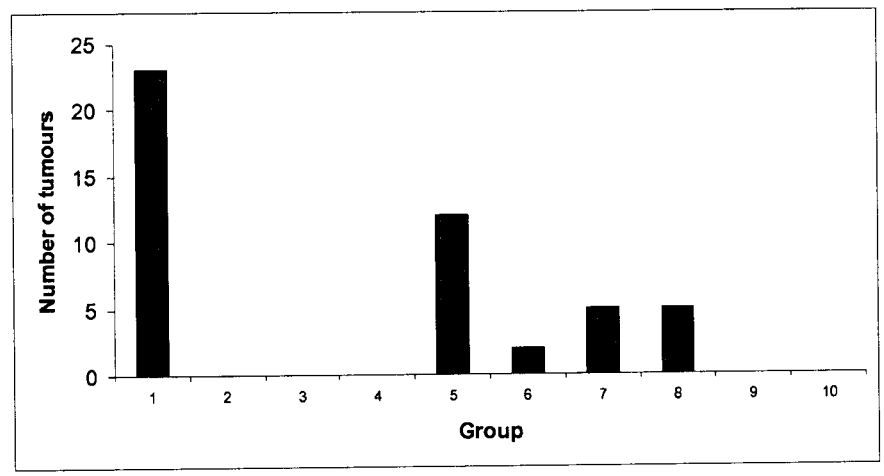
FIG. 2 shows the number of mammary tumours per the following treatment groups (n=12): Group 1 oral treatment with 3.0 ml/kg/day vehicle; Group 2 tamoxifen 1 mg/kg/day orally; Group 3 tamoxifen 2 mg/kg/day orally; Group 4 tamoxifen 3 mg/kg/day orally; Group 5 estetrol (E4) 0.5 mg/kg/day orally; Group 6 E4 1.0 mg/kg/day orally; Group 7 E4 1.5 mg/kg/day orally; Group 8 E4 2.0 mg/kg/day orally; Group 9 E4 2.5 mg/kg/day orally; Group 10 E4 3.0 mg/kg/day orally.

Estetrol and tamoxifen were subsequently tested in a second DMBA trial in rats to evaluate the dose-response relationships in preventing rats from developing mammary tumours. The experimental procedure as set forth in example 3 was used as a prevention study to treat the animals (12 animals per group) for 8 consecutive weeks after tumour induction with oral dosages of either estetrol or tamoxifen. DMBA-exposed rats were randomly assigned to treatment groups, receiving oral treatment as follows:
  Group 1 animals received placebo oral treatment in the form of a single daily dose of 3.0 ml/kg vehicle (20% wt/vol solution of hydroxypropyl-beta-cyclodextrin in water);
  Group 2 animals received tamoxifen orally at a single daily dose of 1 mg/kg;
  Group 3 animals received tamoxifen orally at a single daily dose of 2 mg/kg;
  Group 4 animals received tamoxifen orally at a single daily dose of 3 mg/kg;
  Group 5 animals received estetrol orally at a single daily dose of 0.5 mg/kg;
  Group 6 animals received estetrol orally at a single daily dose of 1.0 mg/kg;
  Group 7 animals received estetrol orally at a single daily dose of 1.5 mg/kg;
  Group 8 animals received estetrol orally at a single daily dose of 2.0 mg/kg;
  Group 9 animals received estetrol orally at a single daily dose of 2.5 mg/kg; and
  Group 10 animals received estetrol orally at a single daily dose of 3.0 mg/kg During the treatment period of 8 weeks, the emergence of palpable tumours and number of tumours were determined weekly. The number of mammary tumours at necropsy is depicted in FIG. 2. As expected, tamoxifen showed an anti-proliferative effect on development of mammary tumours in this prevention study. In none of the tamoxifen groups (1, 2, and 3 mg/kg/day) palpable tumours developed. Oral estetrol treatment (0.5-3.0 mg/kg/day) also showed a dose-dependent inhibition of mammary tumour formation, further confirming its anti-proliferative effect on tumor growth. Furthermore, and as observed for tamoxifen, treatment with 2.5 and 3.0 mg/kg/day estetrol completely protected rats from developing tumours.

Example 5

In order to assess the efficacy of estetrol to reduce the number and size of pre-existing mammary tumours, estetrol was tested in a modified version (therapeutic design) of the 7,12-dimethyl-benz(a)anthracene (DMBA)-induced tumour model in rats. As set forth in example 3, female Sprague-Dawley rats were given 16 mg DMBA at the age of 50 days. Mammary tumour development was allowed to proceed until week 8 after DMBA treatment. Animals were subsequently allocated to one of six groups, receiving 4 weeks daily oral treatment with placebo, tamoxifen or estetrol as follows:
  Group 1 animals received placebo treatment with a single daily dose of 3.0 ml/kg vehicle (20% wt/vol solution of hydroxypropyl-beta-cyclodextrin in water);
  Group 2 animals were surgically castrated and received placebo treatment with 3.0 ml/kg/day vehicle;
  Group 3 animals received tamoxifen at a dose of 1 mg/kg;
  Group 4 animals received estetrol at a dose of 1.0 mg/kg;
  Group 5 animals received estetrol at a dose of 3.0 mg/kg;
  Group 6 animals received estetrol at a dose of 10.0 mg/kg.

The oral doses of estetrol and tamoxifen were selected on the basis of previous findings showing partial or complete suppression of mammary tumour development in a preventive mode of the DMBA model (see example 3 and example 4).

During therapy, the progression or disappearance of palpable mammary tumours and the size of the tumours were determined weekly. At necropsy, tumours were counted, measured and the change from baseline at the start of treatment was calculated.

In vehicle treated animals (n=9) tumour count increased steeply from 16 at the start of treatment to 35 after 4 weeks of therapy. Ovariectomized rats (n=8) showed a 53% decrease in tumour count from 15 at the start of treatment to 7 at necropsy. Despite its efficacy in preventing mammary tumour development immediately after tumour induction with DMBA, tamoxifen at a dose of 1 mg/kg/day did not prevent a further increase in tumour number when administered 8 weeks after DMBA induction. In tamoxifen-treated rats (n=8) the tumour number further increased from 15 at the start of treatment to 19 at necropsy. Interestingly, estetrol dose-dependently reduced the number of pre-existing mammary tumours during the 4 week therapeutic trial. In rats treated with estetrol at a dose of 1 mg/kg/day (n=9), estetrol was marginally effective as indicated by an increase from 16 tumours at the start of treatment to 23 at necropsy. In rats treated with 3 mg/kg/day estetrol (n=9) tumour counts were slightly reduced from 16 at the start of treatment to 15 at necropsy. Furthermore, in rats treated with 10 mg/kg/day estetrol (n=10) tumour number declined from 18 at the start of treatment to 7 at necropsy.

Figure 3:
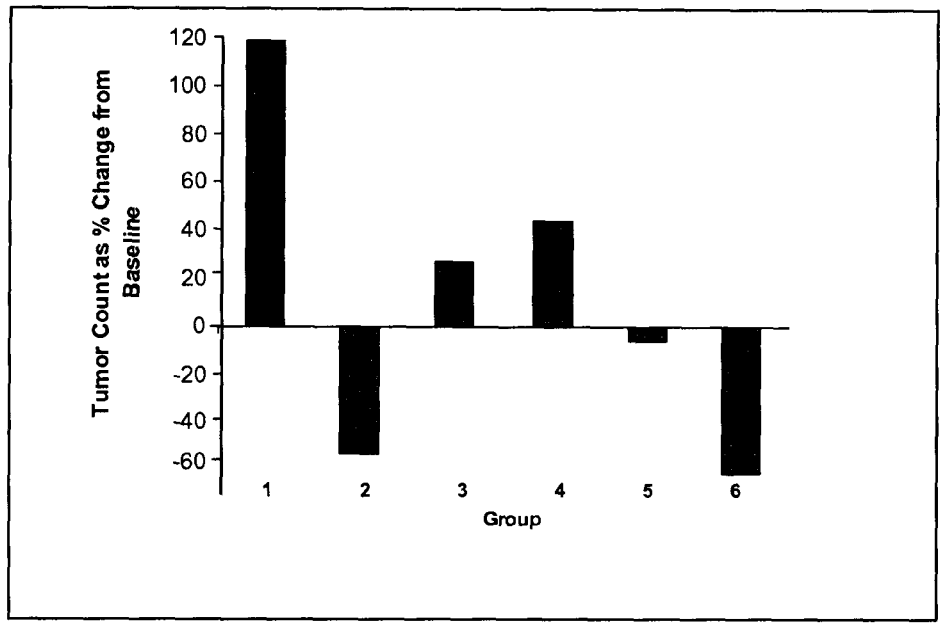
FIG. 3 shows the responsiveness of pre-existing mammary tumours to ovariectomy or 4 weeks oral treatment with tamoxifen or estetrol. Group 1 oral treatment with 3.0 ml/kg/day vehicle; Group 2 surgically castrated animals receiving placebo treatment with 3.0 ml/kg/day vehicle; Group 3 tamoxifen 1 mg/kg/day orally; Group 4 estetrol 1 mg/kg/day orally; Group 5 estetrol 3 mg/kg/day orally; Group 6 estetrol 10 mg/kg/day orally.
Figure 4:
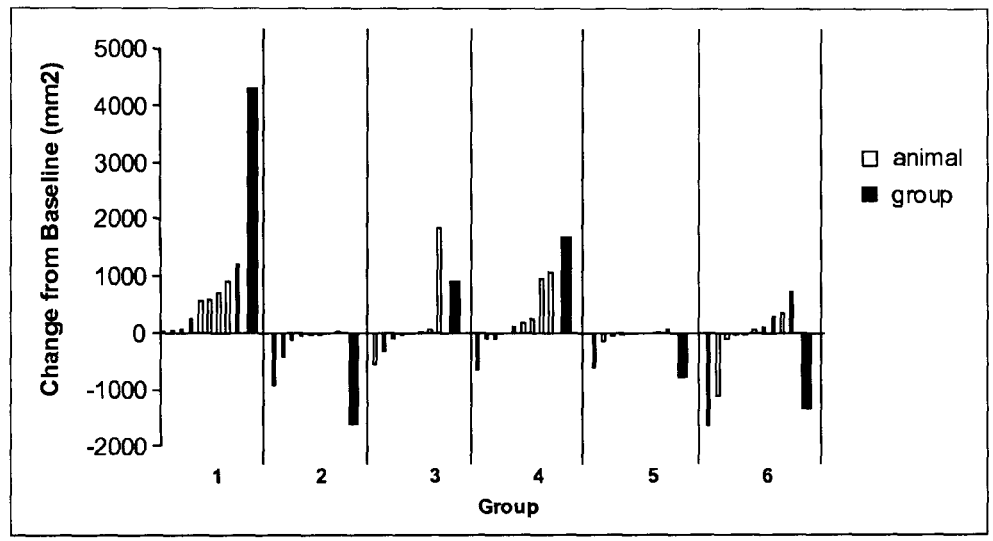
FIG. 4 shows the mammary tumour load per animal (white bars) and per group (black bars) in response to ovariectomy or 4 weeks oral treatment with tamoxifen or estetrol. Group 1 oral treatment with 3.0 ml/kg/day vehicle; Group 2 surgically castrated animals receiving placebo treatment with 3.0 ml/kg/day vehicle; Group 3 tamoxifen 1 mg/kg/day orally; Group 4 estetrol 1 mg/kg/day orally; Group 5 estetrol 3 mg/kg/day orally; Group 6 estetrol 10 mg/kg/day orally.

Hence, from the analysis of the net disappearance of mammary tumours it is evident that the efficacy of estetrol is comparable to ovariectomy. Tamoxifen, at an effective dose to prevent the outgrowth of mammary tumours, was ineffective at later stages in the model to counteract the further development and progression mammary tumours. By expressing the tumour counts as a percentage change from baseline at the start of treatment (FIG. 3), the strong therapeutic efficacy of estetrol becomes clearly evident.

Similarly, by expressing the tumour sizes as percentage change from baseline, estetrol treatment (like ovariectomy) was shown to be effective in causing a dose dependent pronounced tumour size reduction as a net group effect (FIG. 4). Although reduction of tumour size was observed for individually treated rats, the net balance of treating the animals with tamoxifen was less favourable, showing an increase in tumour size as net group effect.

The invention claimed is:

1. A method of treating estrogen-sensitive tumours in a mammal in need thereof, said estrogen-sensitive tumours being selected from the group consisting of breast cancer, uterine cancer, ovarian cancer, endometriosis, and uterine fibroids, comprising orally administering to said mammal a therapeutically effective amount of an estrogenic component selected from the group consisting of:

substances represented by the following formula in which formula $R_1$, $R_2$, $R_3$, $R_4$ independently are a hydrogen atom, a hydroxyl group or an alkoxy group with 1-5 carbon atoms;

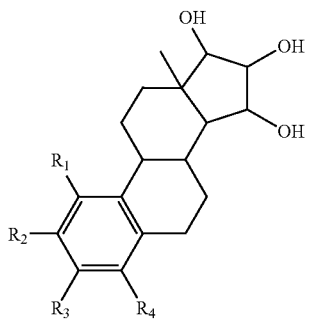

precursors capable of liberating a substance according to the aforementioned formula which precursors are derivatives of the present estrogen substances, wherein the hydrogen atom of at least one of the hydroxyl groups has been substituted by an acyl radical of a hydrocarbon carboxylic, sulfonic acid or sulfamic acid of 1-25 carbon atoms; tetrahydrofuranyl; tetrahydropyranyl; or a straight or branched chain glycosydic residue containing 1-20 glycosidic units per residue; and mixtures of one or more of the aforementioned substances and/or precursors;

said method not comprising administration of a GnRH composition.

2. The method according to claim 1, wherein no more than 3 of $R_1$, $R_2$, $R_3$, $R_4$ are hydrogen atoms.

3. The method according to claim 1, wherein $R_3$ represents a hydroxyl group or an alkoxy group.

4. The method according to claim 1, wherein at least 3 of the groups $R_1$, $R_2$, $R_3$ and $R_4$ represent hydrogen atoms.

5. The method according claim 1, wherein the method comprises the uninterrupted administration of the estrogenic component during a period of at least 30 days.

6. The method according to claim 1, wherein the method comprises oral, transdermal, intravenous or subcutaneous administration of the estrogenic component.

7. The method according to claim 1, wherein the estrogenic component is administered in an amount of at least 1 µg per kg of bodyweight per day.

8. The method according to claim 1, wherein the estrogen-sensitive tumours are selected from the group consisting of breast cancer and uterine cancer.

9. The method according to claim 1, further comprising co-administration of an aromatase inhibitor.

10. A method of treating estrogen-sensitive tumours in a mammal in need thereof, said estrogen-sensitive tumours being selected from the group consisting of breast cancer, uterine cancer, ovarian cancer, endometriosis, and uterine fibroids, comprising orally administering to said mammal a therapeutically effective amount of an estrogenic component as defined in claim 1 in combination with an aromatase inhibitor.

11. The method according to claim 10, wherein no more than 3 of $R_1$, $R_2$, $R_3$, $R_4$ are hydrogen atoms.

12. The method according to claim 10, wherein $R_3$ represents a hydroxyl group or an alkoxy group.

13. The method according to claim 10, wherein at least 3 of the groups $R_1$, $R_2$, $R_3$ and $R_4$ represent hydrogen atoms.

14. The method according claim 10, wherein the method comprises the uninterrupted administration of the estrogenic component during a period of at least 30 days.

15. The method according to claim 10, wherein the method comprises oral, transdermal, intravenous or subcutaneous administration of the estrogenic component.

16. The method according to claim 10, wherein the estrogenic component is administered in an amount of at least 1 µg per kg of bodyweight per day.

17. The method according to claim 10, wherein the estrogen-sensitive tumours are selected from the group consisting of breast cancer and uterine cancer.

18. The method according to claim 10, wherein the aromatase inhibitor is co-administered in an effective amount to suppress blood serum 17β-estradiol level to below 10 pg/ml.

19. A method of treating estrogen-sensitive tumours in a mammal in need thereof, said estrogen-sensitive tumours being selected from the group consisting of breast cancer, uterine cancer, ovarian cancer, endometriosis, and uterine fibroids, comprising orally administering to said mammal a therapeutically effective amount of an estrogenic component as defined in claim 1.

20. The method according to claim 19, wherein no more than 3 of $R_1$, $R_2$, $R_3$, $R_4$ are hydrogen atoms.

21. The method according to claim 19, wherein $R_3$ represents a hydroxyl group or an alkoxy group.

22. The method according to claim 19, wherein at least 3 of the groups $R_1$, $R_2$, $R_3$ and $R_4$ represent hydrogen atoms.

23. The method according to claim 19, wherein the method comprises the uninterrupted administration of the estrogenic component during a period of at least 30 days.

24. The method according to claim 19, wherein the method comprises oral, transdermal, intravenous or subcutaneous administration of the estrogenic component.

25. The method according to claim 19, wherein the estrogenic component is administered in an amount of at least 1 µg per kg of bodyweight per day.

26. The method according to claim 19, wherein the estrogen-sensitive tumours are selected from the group consisting of breast cancer and uterine cancer.

27. The method according to claim 19, comprising co-administration of an aromatase inhibitor.

* * * * *